United States Patent [19]

Watt

[11] 4,150,673
[45] Apr. 24, 1979

[54] CODED ENTRY SYSTEM FOR BLOOD BAG

[75] Inventor: William E. R. Watt, Barto, Pa.

[73] Assignee: Pharmachem Corporation, Bethlehem, Pa.

[21] Appl. No.: 765,295

[22] Filed: Feb. 3, 1977

[51] Int. Cl.² ............................................ A61M 05/14
[52] U.S. Cl. .............................. 128/272; 128/214 D; 128/275; 128/DIG. 24; 222/80; 141/329; 215/321
[58] Field of Search ............... 128/272, 273, 214 D, 128/DIG. 24, 188, 172, 203, 145.8, 142 R, 142.2; 215/321; 222/80, 81; 141/329, 330; 285/24, DIG. 15, 93; 315/22 A; 251/149.6; 137/552; 138/104

[56] References Cited

U.S. PATENT DOCUMENTS

| | | | |
|---|---|---|---|
| 2,721,561 | 10/1955 | Dyche | 401/195 |
| 2,940,183 | 6/1960 | Fromberg | 35/50 |
| 3,127,892 | 4/1964 | Bellamy, Jr. et al. | 128/DIG. 24 |
| 3,170,667 | 2/1965 | Szohatzky | 251/149.6 |
| 3,625,212 | 12/1971 | Rosenberg et al. | 128/214 R |
| 3,951,148 | 4/1976 | Herb | 128/214 D |
| 3,963,026 | 6/1976 | Herb | 128/DIG. 24 |
| 3,986,507 | 10/1976 | Watt | 128/272 |

FOREIGN PATENT DOCUMENTS 1246436  9/1971  United Kingdom .................... 35/22 A

OTHER PUBLICATIONS

Kish, IBM Technical Disclosure Bulletin, vol. 17, No. 7, Dec. 1974, p. 1948.

Primary Examiner—Henry J. Recla

[57] ABSTRACT

A bag for storing blood components consisting of a sterilizable, flexible closed container including a coded inlet-outlet fitment at the top thereof forming part of said closed container, said fitment including at least one inlet consisting of a hollow outward protrusion having on its outer diameter a coded configuration.

6 Claims, 6 Drawing Figures

CODED ENTRY SYSTEM FOR BLOOD BAG

BACKGROUND OF THE INVENTION

1. Field of the Invention

This invention pertains to a bag for storing blood components which is readily adaptable to a variety of uses. More particularly, this invention relates to an improved blood component storage bag with a glycerolizing set which includes inlet and outlet means with specific configurations in combination with a connector having a configuration adapted to sealingly mate with the inlet and outlet means.

2. Discussion of the Prior Art

Sterilizable, flexible closed plastic bags of a variety of shapes and forms have been used as storage containers for blood and various blood components. In most cases, these bags have been adapted to particular uses by virtue of specific inlet and outlet configurations in combination with puncturable diaphragms and integral tubing adapted to the particular use for which the bag was intended. However, these prior art bags do not contain any features which would provide a means for preventing the accidental addition of the wrong additive, medicament or other supplement which are at times required.

It has been proposed to provide color coded entry ports on the blood storage bags so that correct reagents can be added and the decants removed in a proper sequence. However, such color coding would present a problem in having all personnel which handle the container and the reagents familiar with the color code, and that such color coding is standardized throughout the industry. Additional problems in color coding are that colors tend to fade of otherwise change due to atmosphere or by spillage of chemical reagents so that the colors may be unreliable.

U.S. Pat. No. 3,963,026 relates to a bag for storing blood components having features in its construction which may be adapted for use in connection with the present invention. Additionally, this patent discloses the utilization of a Y connector which is adapted to communicate with a glycerin container and with a container of red blood cells.

U.S. Pat. No. 3,951,148 relates to a blood component storage bag and glycerolizing set containing certain features which may be readily adapted for utilization in connection with the present invention. One such feature is the utilization of a connector having a hollow spike which may be inserted into a container, such as a container of red blood cells, to permit free fluid passage through the spike into and from the fluid container.

Therefore, it is a principal object of the present invention to provide a new and improved bag for storing blood components.

Another object of the present invention is to provide a new and improved system for either adding to the blood storage bag or removing portions therefrom in a manner such that the chance of error is substantially reduced.

SUMMARY OF THE INVENTION

Briefly, the above and further objects of the present invention may be realized in accordance with the present invention by providing a storage bag consisting of a sterilizable, flexible closed plastic container with means for hanging the container either in an upright or inverted position, the container further including one or more coded inlet-outlet fitments at the top thereof. Each of the inlet-outlet fitments of the present invention are of a specially selected configuration, that is, round, square, hexagonal, etc., which corresponds in shape to a mating connection of another containers or treatment devices. Preferably, each of the fitments is provided with a removable cap. The fitments may further be constructed according to the structure disclosed in U.S. Pat. No. 3,963,026. That is, the fitment may include an outlet comprising a first hollow outward protrusion with a removable cap and at least one inlet consisting of a second hollow outward protrusion, the second protrusion having on its outer diameter a circumferential raised portion having a configuration so that it can be adapted to sealably engage the inner diameter of a connector from the glycerolizing set.

In one form of the present invention, the bag may be combined with a simple and convenient glycerolizing set which sealably engages one of the inlet protrusions of the bag. The mating portion of the glycerolizing set may be provided with a hollow spike which is utilized to puncture an entrance into a sealed container. The glycerolizing set may also include a metering portion which would regulate the flow rate of fluid into the container.

In the use of the glycerolizing set or any other blood treatment or storage system with the bag of this invention through a flexible resilient tube having an end portion mating with the one or more coded protrusions on the fitment of the bag, a clamp may be provided to ensure the sealing engagement of the end portion of the tube with the inlet or outlet fitment protrusions.

In some glycerolizing sets, at least two flexible resilient tubes are each provided with an external means thereof for restricting fluid flow therein. For example, a sliding valve with a narrow channel therein fits over the tubing with an opening in the valve communicating with the channel usually surrounds the tube during unrestricted fluid passage through the tube. When it is desired to restrict the fluid passage, the valve member is slid over the tube with the narrow constriction forced to collapse the tube so as to restrict fluid flow therethrough. One such means is a roller squeeze valve means as disclosed in U.S. Pat. No. 3,951,148.

For a better understanding of this invention, reference is made to the appended claims and to the following detailed description thereof, taken in conjunction with the drawing in which:

Figure 1:
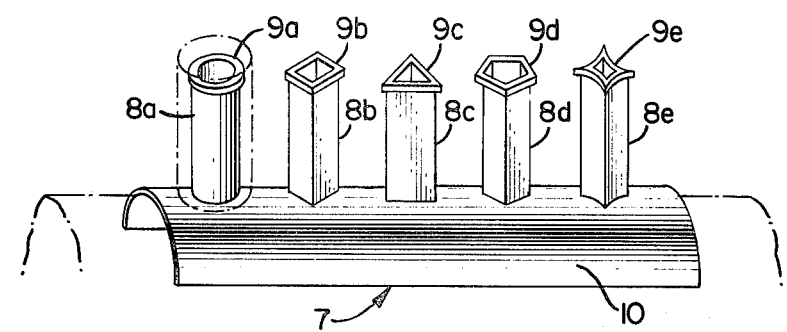
FIG. 1 is a perspective view of the inlet-outlet shape coded fitment utilized in connection with the blood storage bag of the present invention.

With reference to FIG. 1, there is shown a coded port fitment 7 having a series of hollow outward protrusions 8a, 8b, 8c, 8d and 8e, having respectively configured lip portions 9a, 9b, 9c, 9d and 9e. The fitment 7 is of such construction so as to be readily adapted for any standard blood storage bag. Preferably, the fitment 7 has a film portion 10 of heat sealable material which would permit an economical adaptation of existing storage bags for use with the coded filament portion.

Figure 2:
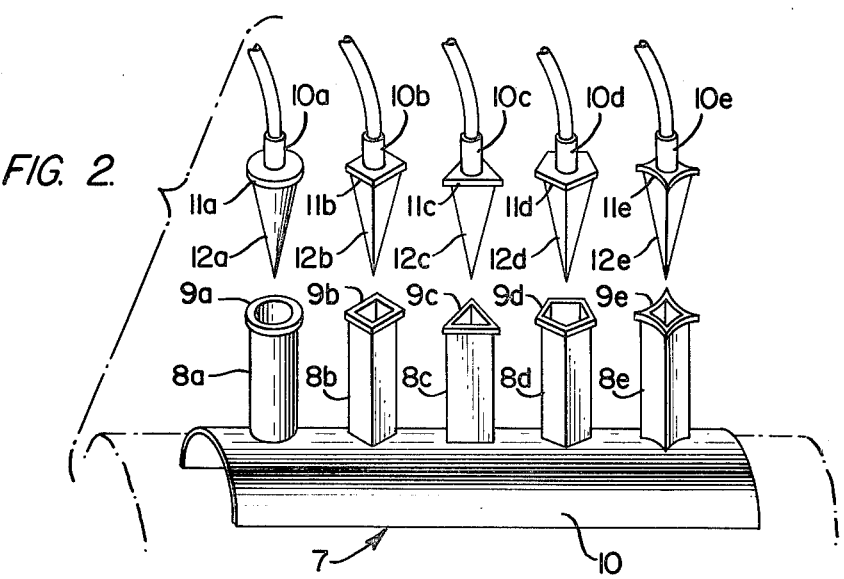
FIG. 2 is a perspective view of another series of inlet-outlet fitment for use in connection with a blood storage bag in accordance with the present invention.

FIG. 2 shows the coded inlet protrusions in combination with mating coded styli 10a, 10b, 10c, 10d, and 10e each with a lip portion 11a, 11b, 11c, 11d and 11e, which closely fits the respectively configured lip portions 9a, 9b, 9c, 9d and 9e. Each of the styli 10a, 10b, 10c, 10d and 10e, may contain conforming hollow spikes 12a, 12b, 12c, 12d and 12e, which enter the respective inlet protrusions so as to puncture the film 10 and provide access into the blood storage bag.

Figure 3:
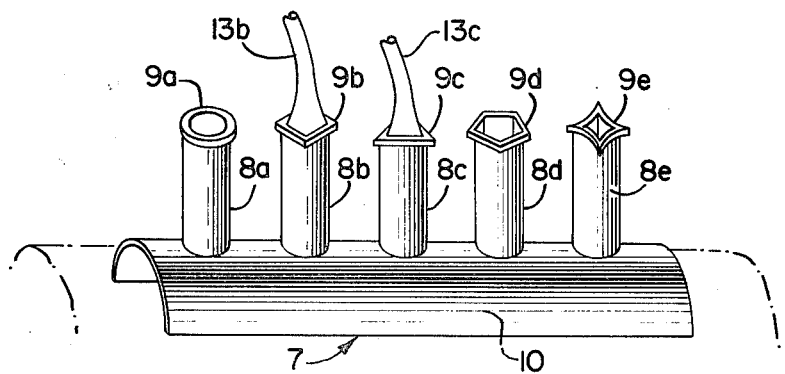
FIG. 3 is a perspective view of the shape coded fitments shown together with matching shape coated spikes used in connection with the present invention.

FIG. 3 illustrates a further embodiment of the present invention wherein the only coded portion of the protrusions 8a, 8b, 8c, 8d and 8e are the lip portions 9a, 9b, 9c, 9d and 9e, which would sealingly engage a matching connector from another source. There is further illustrated that the entry ports may contain the hollow spikes 13b, 13c for puncturing an entrance into another container. Also, as illustrated, the spikes 13b, 13c need not contain the same configuration as the lip portions 9b, 9c provided the container has a cover portion having the same configuration as the lip portion.

Figure 4:
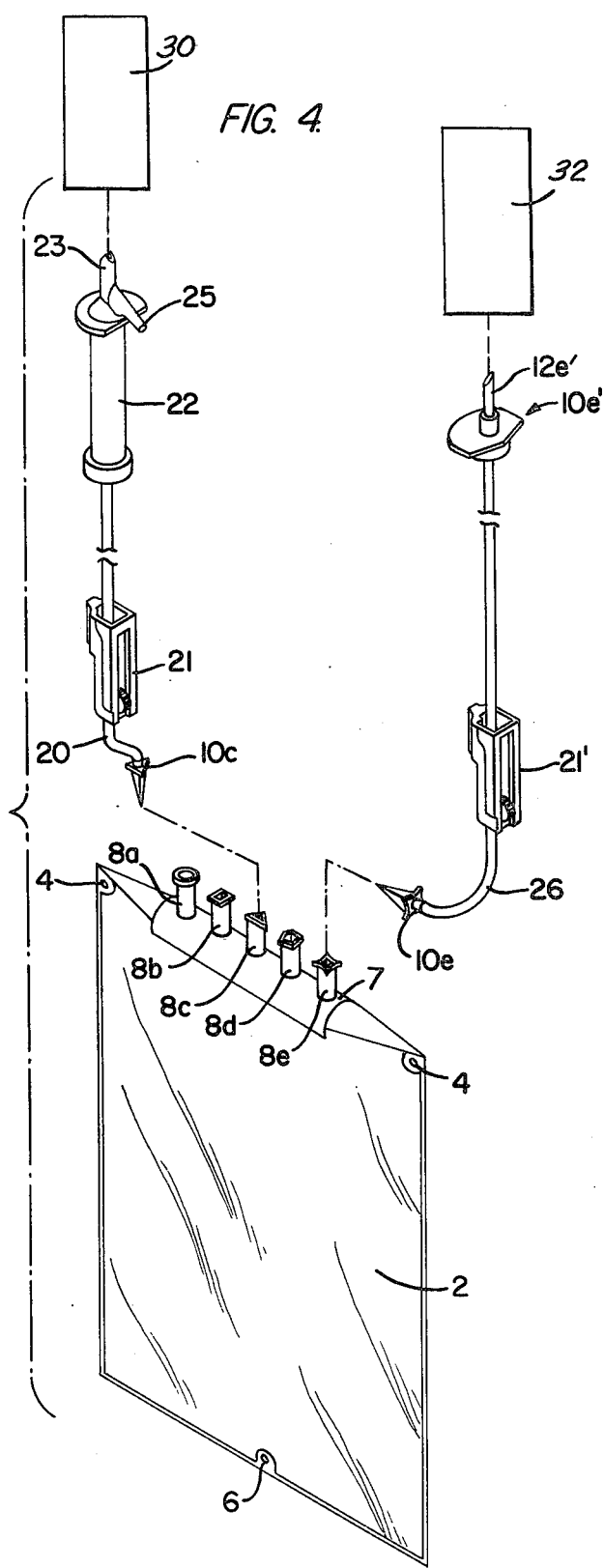
FIG. 4 is a perspective view of the blood storage bag and associated glycerolizing set in accordance with the present invention.

Turning now to FIG. 4, there is shown a sterilizable, flexible plastic bag 2, with means consisting of hanging holes 4 and 6 for hanging the bag either in an upright or inverted position. Bag 2 also includes a closure fitment 7 with the series of hollow outward protrusions 8a, 8b, 8c, 8d, 8e with their respectively configured lip portions.

As seen in FIG. 4, the tube 20 is connected to a stylus 10c. The tube 20 has mounted thereon a valve member 21 providing a controllable fluid flow restrictor as may be required in the functioning or use of the apparatus. The tube 20 further communicates with a drip chamber 22, consisting of a relatively large diameter transparent collapsible symmetrical member attached to a hollow puncturing spike 23, in which is incorporated an integral air vent 25.

A second flexible tube 26 is connected to stylus 10e for entry into protrusion 8e. The tube 26 has mounted thereon a second valve means 21'. The tube 26 is further connected to a second matching stylus 10e' with a puncturing hollow spike 12e'.

In the use of the bag 2 and glycerolizing set according to the present invention, particularly in the use of the glycerolizing set in conjunction with the use of the bag 2 as a free storage container for red blood cells, fluid flow in tube 20 is first restricted by valve means 21 and drip chamber 22 is partially collapsed, such as by squeezing it. Spike 23 is then inserted into a resilient closure cap of a container 30 of glycerin or other suitable red blood cell preservative and the pressure on drip chamber 22 is relaxed, whereby glycerin is drawn into it at the same time air is drawn into the glycerin container through the air vent 25 of the spike 23. Spike 12e' is inserted in the container 32 of red blood cells and, with valve means 20 and 21' in an open position and with both the stylus 10c and 10e inserted in their respective entry protrusions of bag 2, the glycerin container is raised or the red blood cell container is lowered so that the glycerin enters the red blood cell container. It should be understood that in this particular step the bag 2 is typically in the inverted position, i.e., hung by hanging hole 6. After about 100 milliliters of glycerin has passed into the red blood cell container, fluid flow is constricted by means of valve means 21 and 21'. After permitting the partially glycerolized red blood cells to equilibrate for five to ten minutes, the glycerin container and the red blood cell container are raised above the bag 2, valve means 21' is opened and the contents of the red blood cell storage container are permitted to flow into bag 2. Valve means 21 is then opened and the remainder of the glycerin passes into bag 2. The glycerolizing set may then be sealed from the bag 2 by any conventional means and separated whereupon the treated red blood cells in bag 2 are ready for free storage.

Figure 5:
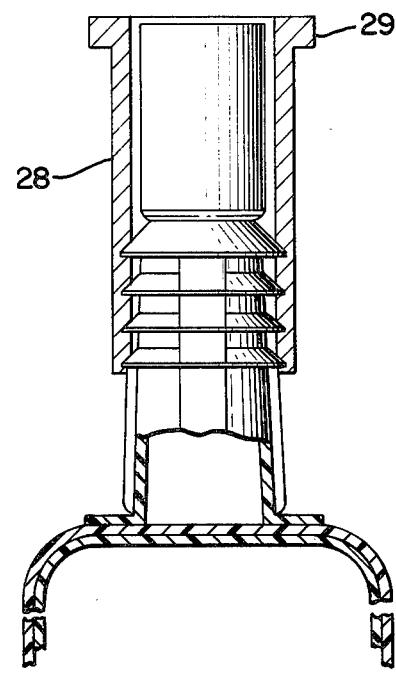
FIGS. 5 and 6 are enlarged views, partially in section, of the outlet opening and associated individual shape coded overlay in accordance with a further embodiment of the present invention.
Figure 6:
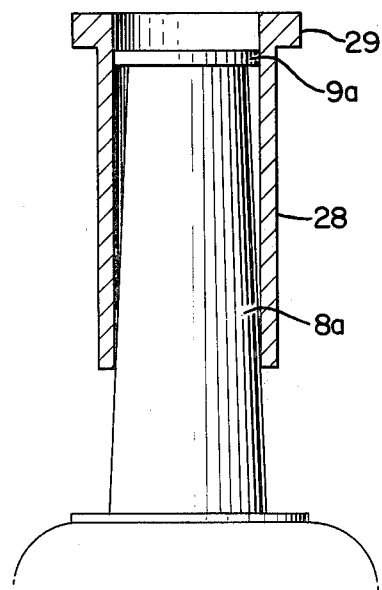

FIGS. 5 and 6 illustrate a further embodiment of the present invention wherein the coded portion is a separate unit which is utilized so as to adapt any bag having a conventional port to the coded system. The overlying coded member 28 contains the coded configuration 29. The overlying coded member 28 may be reusable and formed in any manner so as to be held by the conventional inlet protrusion, such as being of elastic means, being internally threaded, or the like.

While this invention has been described with respect to specific embodiments thereof, it should be understood that this invention is not limited to these embodiments and that the appended claims are intended to include these and other features and embodiments as may be devised by those skilled in the art which are nevertheless within the spirit and scope of this invention.

We claim:

1. In a bag for storing blood components consisting of a sterilizable flexible closed container, the improvement which comprises: an inlet-outlet fitment at the top thereof and forming a part of said closed container so that said container remains sealed after said fitment is attached, said fitment having at least one inlet consisting of a hollow outward protrusion having on its outer diameter a shape-coded configuration, a fluidic connector having a shape-coded configuration corresponding to the shape-coded configuration of said protrusion and being removably and matably sealed in said protrusion; said connector having means for piercing said fitment and said container when inserted in said protrusion, whereby matably sealing said connector with said protrusion causes the piercing means to puncture said fitment and said bag and provide access therein.

2. The bag according to claim 1 including a plurality of hollow outward protrusions, each of said protrusions having a different configuration.

3. The bag according to claim 1 wherein each hollow outward protrusion has a coded configuration only at the upper and outer portion thereof.

4. The bag according to claim 1 including a second container having an outlet connected to said correspondingly coded connector for matably and removably sealing with said correspondingly coded protrusion on said fitment, said connector including a hollow piercing spike for puncturing said fitment and said container when inserted into the respective protrusion so as to form a communication between said bag and said second container.

5. The bag according to claim 1 including a glycerolizing set having at least one flexible tube connected to said correspondingly coded connector having a hollow spike for puncturing said fitment and said flexible container and sealingly and removably mating with said configuration coded protrusion.

6. A means for coding an inlet-outlet fitment, having at least one protrusion, of a sealed blood storage bag comprising a coded member removably engaged over one of the protrusions of said fitment, said member having at its upper portion a configuration coded portion a fluidic connector having a coded configuration corresponding to the coded configuration of said fitment and being removably and matably sealed in said protrusion, said connector having piercing means for puncturing said fitment and said bag, whereby when said connector is matably sealed in said protrusion, said piercing means punctures said fitment and said bag and thereby a proper fluid may be added into said storage bag from another container only through said correspondingly configurated coded mating connector.

* * * * *